(12) United States Patent
Tsukada et al.

(10) Patent No.: US 11,610,701 B2
(45) Date of Patent: Mar. 21, 2023

(54) COMPOSITE WIRING, SIGNAL ACQUISITION MEMBER, AND PRODUCTION METHOD OF SAME

(71) Applicant: NIPPON TELEGRAPH AND TELEPHONE CORPORATION, Tokyo (JP)

(72) Inventors: Shingo Tsukada, Atsugi (JP); Hiroshi Nakashima, Atsugi (JP)

(73) Assignee: NIPPON TELEGRAPH AND TELEPHONE CORPORATION, Tokyo (JP)

(*) Notice: Subject to any disclaimer, the term of this patent is extended or adjusted under 35 U.S.C. 154(b) by 69 days.

(21) Appl. No.: 16/757,909

(22) PCT Filed: Nov. 13, 2018

(86) PCT No.: PCT/JP2018/041954
§ 371 (c)(1),
(2) Date: Apr. 21, 2020

(87) PCT Pub. No.: WO2019/098184
PCT Pub. Date: May 23, 2019

(65) Prior Publication Data
US 2020/0343020 A1 Oct. 29, 2020

(30) Foreign Application Priority Data

Nov. 15, 2017 (JP) .............................. JP2017-220480

(51) Int. Cl.
*H01B 7/282* (2006.01)
*A61B 5/00* (2006.01)
(Continued)

(52) U.S. Cl.
CPC ........... *H01B 7/282* (2013.01); *A61B 5/0006* (2013.01); *H01B 7/04* (2013.01); *H01R 4/18* (2013.01)

(58) Field of Classification Search
CPC .......... H01B 7/06; H01B 7/282; A61B 5/256; A61B 5/273; H01R 4/18; H01R 4/20; H01R 4/70
See application file for complete search history.

(56) References Cited

U.S. PATENT DOCUMENTS 5,278,354 A * 1/1994 Lhomme ................... H01R 4/72
174/DIG. 8
5,422,438 A * 6/1995 Lamome ................... H01R 4/70
174/76
(Continued)

FOREIGN PATENT DOCUMENTS

CN 2837581 Y 11/2006
CN 1911167 A 2/2007
(Continued)

OTHER PUBLICATIONS

European Office Action in counterpart EP18877951.6, dated Feb. 14, 2022.
(Continued)

*Primary Examiner* — Paresh Paghadal
(74) *Attorney, Agent, or Firm* — Harness, Dickey & Pierce, P.L.C.

(57) ABSTRACT

A composite wiring includes: elastic wiring comprising an elastic tube, a conductor wire disposed inside the tube, and fixing portions that fix the conductor wire and the tube together at both ends of the tube in the lengthwise direction thereof, the length of the conductor wire between the fixing portions when the tube is in an unextended state being longer than the length of the tube between the fixing portions; other wiring separate from the elastic wiring; and a connection
(Continued)

member that connects the conductor wire of the elastic wiring and a conductor wire of the other wiring by caulking in a state of being brought into contact with each other, the connection member having an interior section sealed in a watertight manner with a sealing material.

6 Claims, 7 Drawing Sheets

(51) Int. Cl.
  *H01B 7/04* (2006.01)
  *H01R 4/18* (2006.01)

(56) References Cited

U.S. PATENT DOCUMENTS

| | | | |
|---|---|---|---|
| 6,341,504 | B1 | 1/2002 | Istook |
| 6,666,732 | B1 * | 12/2003 | Endacott ............... H01R 4/187 |
| | | | 439/730 |
| 2004/0168315 | A1 | 9/2004 | Onuma |
| 2007/0088227 | A1 | 4/2007 | Nishimura |
| 2013/0309903 | A1 * | 11/2013 | Iio ...................... H01R 13/5216 |
| | | | 439/523 |
| 2016/0126709 | A1 | 5/2016 | Maeda |

FOREIGN PATENT DOCUMENTS

| | | | | |
|---|---|---|---|---|
| CN | 206619432 U | 11/2017 | | |
| JP | S57-017007 U | 1/1982 | | |
| JP | S59-118228 U | 8/1984 | | |
| JP | H05-043420 U | 6/1993 | | |
| JP | 2939740 B1 | 8/1999 | | |
| JP | 2004200094 A | 7/2004 | | |
| JP | 2009087855 A | 4/2009 | | |
| JP | 2017050155 A | 3/2017 | | |
| JP | 2017121442 A | 7/2017 | | |
| JP | 2017191774 A | 10/2017 | | |
| WO | WO-2011001840 A1 * | 1/2011 | ........... | H01R 13/504 |
| WO | WO-2014129603 A1 | 8/2014 | | |
| WO | WO-2015138515 A1 | 9/2015 | | |

OTHER PUBLICATIONS

T. Ogasawara et al., NTT Technical Journal, "Application Development of Wearable Electrode Inner Technology", 26 (11), pp. 16 to 20, Nov. 2014.

International Search Report (in English and Japanese) issued in International Application PCT/JP2018/041954, dated Feb. 5, 2019; ISA/JP.

* cited by examiner

COMPOSITE WIRING, SIGNAL ACQUISITION MEMBER, AND PRODUCTION METHOD OF SAME

CROSS-REFERENCE TO RELATED APPLICATIONS

This application is a 371 National Phase of International Application No. PCT/JP2018/041954, filed on Nov. 13, 2018, which claims priority to Japanese Application No. 2017-220480, filed on Nov. 15, 2017. The entire disclosures of the above applications are incorporated herein by reference.

TECHNICAL FIELD

The present invention relates to a composite wiring, a signal acquisition member, and a production method thereof.

BACKGROUND ART

When a heart attack, convulsive cramping of skeletal muscle, and convulsion seizures due to epilepsy and the like occur, prompt action is required. Recent years have seen increasing opportunities for middle-aged and senior citizens to exercise in pools and hot spring facilities for rehabilitation and health promotion, so it is also necessary to respond quickly to accidents during exercise. As a method for detecting such seizures and accidents, there is a method of acquiring a biometric signal such as an electrocardiogram or electromyogram using a wearable bio-signal acquisition device such as a belt-type or garment-type wearable bio-electrode (Non-Patent Document 1). In recent years, wearable bio-signal acquisition devices have also used in the field of sports science and play an important role therein. For example, a bio-signal such as an electromyogram is obtained while swimming using a swimsuit-type wearable bioelectrode.

In wearable biosignal acquisition devices, when wire-wire connections or wire-electrode connections are not sufficiently waterproof, short circuiting of the wiring and electrodes or a deterioration in insulation may result from the ingress of an electrolytic solution due to sweating or getting wet from water, leading to signal loss and signal attenuation. In addition, water may enter the wiring from the connection portion during washing or swimming, and the water remaining in the wiring may come out from the connection portion the next time the user wears the device, leading to a discomfort. In addition, when copper wire or tin-plated copper wire is used for the wiring, insufficient waterproofing of the connection portion could lead to deterioration of the signal acquisition performance due to increased contact resistance, as well as green-blue discoloration of the fabric of the wearable device.

PRIOR ART DOCUMENTS

Non-Patent Documents

[Non-Patent Document 1] "Application and development of wearable electrode inner technology", NTT Technical Journal, vol. 26, no. 11, pp. 16-20, November 2011.

SUMMARY OF THE INVENTION

Problems to be Solved by the Invention

An object of this invention is to provide a composite wiring having excellent waterproofness of the connection portion between wirings, a signal acquisition member with excellent waterproofness of the connection portion between wiring and an electrode, and production methods thereof.

Means for Solving the Problems

A composite wiring according to one embodiment of the present invention has elastic wiring provided with an elastic tube, a conductor wire disposed inside the tube, and fixing portions that fix the conductor wire and the tube together at both ends of the tube in the lengthwise direction thereof, the length of the conductor wire between the fixing portions when the tube is in an unextended state being longer than the length of the tube between the fixing portions; other wiring separate from the elastic wiring; and a connection member that connects the conductor wire of the elastic wiring and a conductor wire of the other wiring by caulking in a state of being brought into contact with each other, the connection member having an interior section sealed in a watertight manner with a sealing material.

In the composite wiring according to one embodiment of the present invention, the connection member may be a crimping sleeve, and the crimping sleeve may connect the conductor wire of the elastic wiring and the conductor wire of the other wiring by caulking the conductor wire of the other wiring inserted in an end portion of the tube of the elastic wiring from the periphery of the tube of the elastic wiring.

In the composite wiring according to one embodiment of the present invention, the sealing material may be a non-curing elastic sealing material.

In the composite wiring according to one embodiment of the present invention, the fixing portions may each includes a caulking member provided with a male member provided with a first flat plate portion and a fitting convex portion that is provided on the first flat plate portion, and a female member provided with a second flat plate portion and a fitting concave portion that is provided on the second flat plate portion, and in a state of the fitting convex portion and the fitting concave portion being fitted together, the conductor wire and the tube may be caulked by the first flat plate portion and the second flat plate portion, and a protrusion may be formed in the female member.

In the elastic wiring according to one embodiment of the present invention, the fixing portions may each includes a caulking member, with the caulking member having a male member having a flat plate portion and a spike extending substantially perpendicularly from the flat plate portion, and a ring-shaped female member fixed to the male member by being crimped to the spike, and by fixing the female member to the male member, the conductor wire and the tube may be caulked by the flat plate portion and the female member, and a recess may be formed in the ring-shaped central portion of the female member.

A method for producing the composite wiring according to one embodiment of the present invention, the method including a step of supplying the sealing material to a portion where the conductor wire of the elastic wiring and the conductor wire of the other wiring are in contact with each other, and a step of caulking the connection portion.

A signal acquisition member of one embodiment of the present invention provided with wiring and an electrode that is connected to a conductor wire of the wiring by caulking, wherein a connection portion between the conductor wire and the electrode is sealed with a sealing material in a watertight manner.

A method for producing the signal acquisition member according to one embodiment of the present invention, the method including a step of supplying the sealing material to a contact portion of the conductor wire and the electrode and a step of forming the connection portion by caulking the contact portion.

Advantageous Effects of the Invention

According to the present invention, a composite wiring with excellent waterproofing performance of the connection portion between wirings, and a signal acquisition member with excellent waterproofness of the connection portion between wiring and an electrode are obtained.

EMBODIMENTS FOR CARRYING OUT THE INVENTION

The dimensions and the like illustrated in the following description are merely examples, and the present invention is not necessarily limited thereto, and can be appropriately modified and implemented within a scope of not altering the gist thereof.

[Composite Wiring]

A composite wiring according to the first aspect of the present invention is provided with an elastic wiring described below and an extension wiring (other wiring) other than the elastic wiring, with a conductor wire of the elastic wiring and a conductor wire of the extension wiring being in mutual contact, and a connection portion therebetween being sealed in a watertight manner with a sealing material. The elastic wiring is a wiring in which a conductor wire is arranged within an elastic tube, and the conductor wire and the tube are fixed at both end portions of the tube in the lengthwise direction thereof so that the length of the conductor wire between fixing portions when the tube is in an unextended state is longer than the length of the tube between the fixing portions.

Hereinafter, the composite wiring according to the first aspect of the present invention will be described by illustrating an example.

Figure 1:
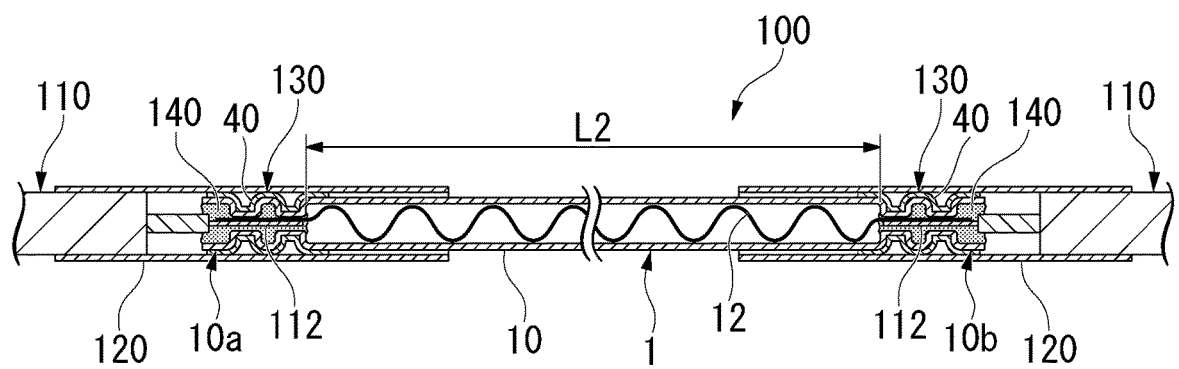
FIG. 1 is a cross-sectional view showing a composite wiring according to an embodiment of the present invention.
Figure 2:
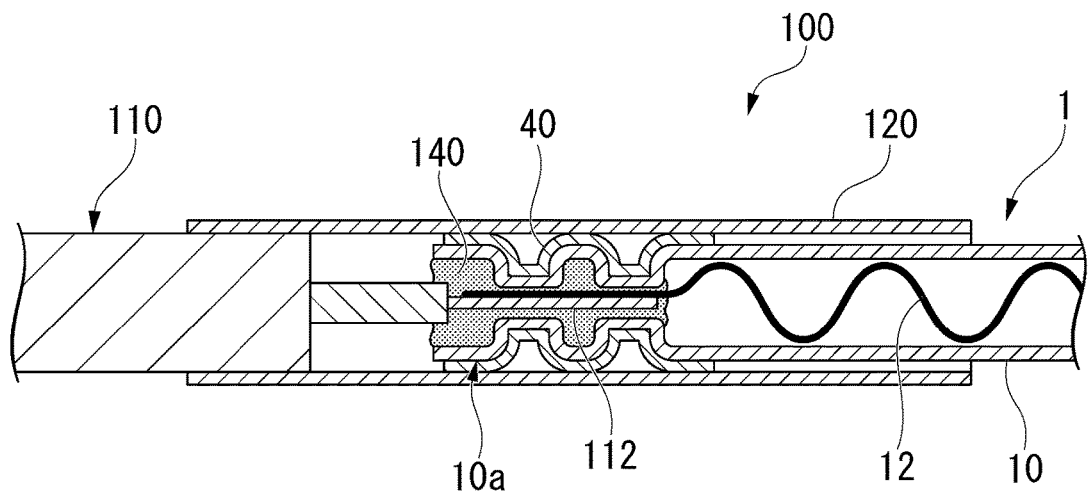
FIG. 2 is an enlarged cross-sectional view showing a connection portion of the composite wiring in FIG. 1.

As shown in FIGS. 1 and 2, a composite wiring 100 according to the present embodiment is provided with an elastic wiring 1, an extension wiring (other wiring) 110 other than the elastic wiring 1, a connection member 40, and cover members 120, 120. In the composite wiring 100, each connection portion 130 between the elastic wiring 1 and the extension wiring 110 is respectively caulked by the connection member 40.

The elastic wiring is provided with a tube 10 and a conductor wire 12.

The conductor wire 12 is arranged within the tube 10 so as to extend from a first end portion 10a to a second end portion 10b of the tube 10 in the lengthwise direction thereof. In the elastic wiring 1, the conductor wire 12 and the tube 10 are fixed by caulking by the connection members 40 at both ends of the tube 10 in the lengthwise direction, namely, the first end portion 10a side and the second end portion 10b side. In this example, the connection member 40 has a role of caulking and connecting the elastic wiring 1 and the extension wiring 110 and a role of caulking and fixing the conductor wire 12 and the tube 10 in the elastic wiring 1.

The tube 10 has elasticity. That is, the tube 10 is a tube that hardly breaks when extended by application of a load in the lengthwise direction thereof, and has little residual displacement upon contracting when the load is removed. The elasticity of the tube 10 can be adjusted by the material and thickness of the tube 10.

As a material for forming the tube 10, an insulating material having elasticity can be used. For example, various elastomers such as silicone rubber, urethane rubber, natural rubber, isoprene rubber, butadiene rubber, styrene-butadiene rubber, chloroprene rubber, nitrile rubber, polyisobutylene, ethylene propylene rubber, chlorosulfonated polyethylene, acrylic rubber, fluorine rubber, and epichlorohydrin rubber can be used. As a material for forming the tube 10, silicone rubber is preferable from the viewpoint of heat resistance. As a material for forming the tube 10, one type may be used alone, or two or more types may be used in combination.

The extension at breakage of the tube 10 is preferably 25 to 300%, and more preferably 50 to 150%. If the extension at breakage of the tube 10 is equal to or greater than the lower limit of the above range, the elasticity of the elastic wiring 1 is improved and the sense of discomfort is further reduced. If the extension at breakage of the tube 10 is less than or equal to the upper limit of the above range, it is possible to avoid breakage and short circuiting of the wiring due to stress applied to the wiring as a result of stretching of the fabric when changing clothes.

The extension at breakage of the tube is measured according to JIS K-7127 (1999).

The inner diameter and the outer diameter of the tube 10 are not particularly limited, and may be set as appropriate so that the conductor wire 12 can be disposed in the tube 10.

For example, the inner diameter of the tube 10 can be 0.1 to 10 mm, and the outer diameter can be 0.2 to 12 mm.

The thickness of the tube 10 is preferably 0.1 to 1 mm, and more preferably 0.2 to 0.6 mm. If the thickness of the tube 10 is equal to or greater than the lower limit of the above range, sufficient strength can be easily obtained.

If the thickness of the tube 10 is less than or equal to the upper limit of the above range, excellent elasticity is easily obtained.

As a material for forming the conductor wire 12, materials generally used for conductor wires can be used, and examples thereof include stainless steel (SUS), enamel, gold, platinum, and iridium. Among these, SUS is preferable as a material for forming the conductor wire 12 because it is not easily rusted, has excellent heat resistance, and can be washed when applied to clothing. The material for forming the conductor wire 12 may be one type or two or more types.

In the present invention, a combination of a tube formed of silicone rubber and a conductor wire formed of SUS thread is particularly preferable.

The form of the conductor wire 12 is not particularly limited, and for example may have the form of a single fiber or may have the form of a twisted thread in which a plurality of fibers are twisted together. In particular, the conductor wire 12 being in the form of interweaving strands is preferable from the standpoint of the conductor wire 12 having less of a tendency to spiral and become tangled in the tube 10 in an unextended state, and so can exist in a more stable state and allow smooth expansion and contraction of the elastic wiring 1.

The thickness of the conductor wire 12 can be set as appropriate, for example, 0.01 to 10 mm.

Note that when the conductor wire 12 is a twisted thread composed of a plurality of wires, the outer diameter thereof is defined as the thickness of the conductor wire 12.

An insulating coat may be applied to the surface of the conductor wire 12. Since the surface of the conductor wire 12 is coated with insulation, the impedance change accompanying expansion and contraction is reduced. As the insulating material used for the insulating coating, publicly known materials can be used. For example, polyurethane, polyesterimide, polyamideimide, poiimide, PVC (polyvinyl chloride mixture), PE (polyethylene) fluororesin, TUFRET (tufflet), and rubber can be used. As a method of insulating coating, a publicly known method can be adopted.

The conductor wire 12 may be coated with a lubricant such as silicone oil or a rust preventive material.

In the elastic wiring 1, the conductor wire 12 is arranged and fixed in the tube 10 so that the length L1 of the conductor wire 12 between the fixing portions is longer than the length L2 of the tube 10 between the fixing portions when the tube 10 is not extended.

Figure 3:
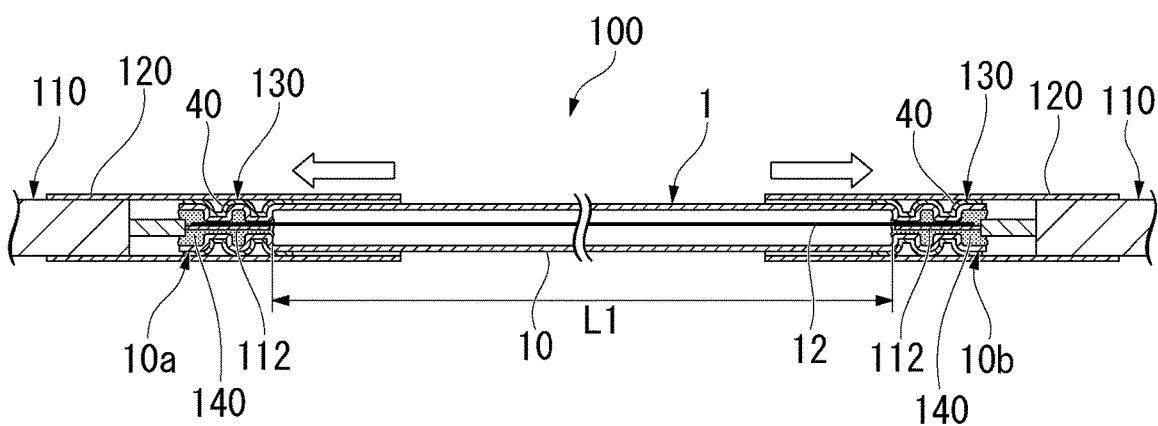
FIG. 3 is a cross-sectional view showing a state in which the composite wiring of FIG. 1 is extended in the lengthwise direction.

Note that when the tube 10 is extended by pulling in the lengthwise direction thereof, putting the conductor wire 12 in a state of being linearly tensioned as shown in FIG. 3, the length L1 of the conductor wire 12 between the fixing portions corresponds to the distance between the fixing portions by the connection members 40 at both ends.

Because the length L1 of the conductor wire 12 between the fixing portions is longer than the length L2 of the tube 10 between the fixing portions, the conductor wire 12 takes on a shape having curves or bends so as to have a spiral shape or a zigzag shape in the tube 10 when the tube 10 is not extended. Thus, even if the conductor wire 12 itself is not substantially elastic, the conductor wire 12 is not strained by curving or bending within the tube 10 and has slack allowing extension in the lengthwise direction thereof.

Therefore, the elastic wiring 1 can be extended by being pulled until the conductor wire 12 becomes linear as shown in FIG. 3, and when the tensile load is released, the conductor wire 12 contracts due to the elasticity of the tube 10 as shown in FIG. 1.

Further, in the expansion and contraction of the elastic wiring 1, since the conductor wire 12 either has a shape with curves or bends or is linear, there is little impedance fluctuation of the conductor wire 12 accompanying the extension compared to a conductor wire including, for example, a conductive material mixed with an elastomer.

The ratio L1/L2 of the length L1 of the conductor wire 12 between the fixing portions to the length L2 of the tube 10 between the fixing portions in a state where the tube 10 is not extended is preferably 1.1 to 5, with 1.2 to 2.5 being more preferable. If the ratio L1/L2 is equal to or greater than the lower limit of the above range, excellent elasticity is easily obtained, and a sense of discomfort is further minimized. If the ratio L1/L2 is below the upper limit of the above range, production of the elastic wiring 1 will be easy and productivity will become high.

The periphery of the conductor wire 12 in the tube 10 may be in a state in which air is present or in a state in which a liquid is filled therein. A state in which is air present is preferable from the standpoint of ease of production of the elastic wiring 1.

The liquid to be filled around the conductor wire 12 in the tube 10 may be any liquid that does not inhibit movement of the conductor wire 12 within the tube 10 and that does not degrade the conductor wire 12, with examples including oil-based oil, silicone oil, glycerin, glycerol and the like.

More specifically, an example will be described in which a silicon tube having an outer diameter of 2 mm and a wall thickness of about 0.2 mm is used as the tube 10 and a SUS (Steel Use Stainless) wire having a length of about 140 cm is used as the conductor wire 12. The thickness of the SUS wire (SUS304) is 12 μm and the mass is 0.22 g/m. The SUS wire is covered with the silicon tube, both ends of the silicon tube and the SUS wire are fixed, and the length of the tube and the SUS wire are contracted about 50%.

The elastic wiring 1 obtained in this way had a wire diameter of 2.5 mm and a length of 60 cm in a state of tension not being applied. When the elastic wiring 1 was tensioned in the lengthwise direction to be fully extended, the length became 136 cm. The tension (initial motion sensitivity) when this elastic wiring 1 starts to be extended was 0.03 Newton (N), and the tension required for complete extension (maximum tension at the time of extension) was 1.2 N. The DC resistance value of the SUS wire of the elastic wiring 1 was 30.5Ω, and no change in the resistance value due to the extension was observed. When the elastic wiring 1 was completely extended and then the tension was released, the wire diameter was 2.5 mm and the length returned to 60 cm.

As described above, the elastic wiring 1 can be extended with a small tension. Accordingly, when worn by the subject together with clothes, the elastic wiring 1 extends without a sense of discomfort like a rubber string. Upon being extended with movement of the body when used as a wearable wiring, the elastic wiring 1 does not exert tension on a connected bioelectrode. Therefore, there is no shifting of the bioelectrode from the mounted position, and distortion of the signal obtained from the bioelectrode hardly occurs.

The wire diameter of this elastic wiring 1 is 2.5 mm, which is thinner than conventional cables. Moreover, by using the silicon tube as the tube, this elastic wiring 1 is flexible and soft to the touch. The elastic wiring 1 is attached to clothing and, even when in direct contact with skin, does not produce discomfort so is suitable for long-term biomedical measurement. The elastic wiring 1 using silicon and SUS wire is resistant to heat and chemicals, can be washed with a washing machine, and can be dried with a drying machine or a dryer.

The extension wiring (other wiring) 110 is not particularly limited, and a publicly known wiring can be used. A conductor wire 112 of the extension wiring 110 may be a conductor wire using copper wire or a tin-plated copper wire.

In the composite wiring 100, the conductor wire 12 of the elastic wiring 1 and the conductor wire 112 of the extension wiring 110 are caulked and connected by the connection member 40 in a state of being in contact with each other. Further, the connection portion 130 caulked by the connection member 40 is sealed in a watertight manner by a sealing material 140.

Specifically, in this example, as shown in FIG. 2, the conductor wire 112 drawn from the extension wiring 110 is inserted into the tube 10 of the elastic wiring 1 from the first end portion 10a side, whereby the conductor wire 12 of the elastic wiring 1 and the conductor wire 112 of the extension wiring 110 are in contact with each other. In the connection portion 130, the periphery of the conductor wire 12 of the elastic wiring 1 and the conductor wire 112 of the extension wiring 110 in the tube 10 is sealed in a watertight manner by being filled with the sealing material 140. Thereby, the connection portion 130 has excellent waterproofness.

The connection member 40 may be any member that can caulk and connect the conductor wire 12 of the elastic wiring 1 and the conductor wire 112 of the extension wiring 110, and a publicly known crimping terminal can be used. In particular, as the connection member 40, a crimping tube (crimping sleeve) is preferable.

In this example, a crimping tube (crimping sleeve) is used as the connection member 40, and the conductor wire 12 of the elastic wiring 1 and the conductor wire 112 of the extension wiring 110 are brought into contact within the connection member 40.

The connection member 40 is partially crushed and crimped, whereby the conductor wires are caulked together with the tube 10 of the elastic wiring 1 to form the connection portion 130. In the present invention, in this manner, in the crimping tube, it is preferable that the conductor wire of the extension wiring be inserted into the end of the tube of the elastic wiring, the conductor wire of the elastic wiring and the conductor wire of the extension wiring be brought into contact with each other, and the connection portion be formed by caulking of the conductor wires with the tube of the elastic wiring by the crimping tube. Thereby, the waterproofness of the connection portion between the elastic wiring and an extension wiring becomes more excellent.

The sealing material 140 is not particularly limited as long as the sealing material can ensure waterproofness, but from the viewpoint of easily following the movement of the elastic wiring 1 even after curing, and suppressing a drop in waterproofness with the appearance of cracks, gaps, and the like, a non-curing elastic sealing material is preferable.

Examples of the material for forming the elastic sealing material include rubber such as silicone and fluoro rubber, polyethylene, and acetic acid resin emulsion.

From the viewpoint of workability, it is preferable that the sealing material 140 cure after being supplied to the connection portion 130 in a liquid state. Further, in terms of easily preserving the elasticity of the elastic wiring 1, it is preferable that the sealing material 140 remain in the vicinity of the connection portion 130 in the tube 10 as much as possible, and that the sealing material 140 not spread from the connection portion 130 toward the center part side in the length direction. In this respect, it is preferable to use a sealing material having a certain degree of viscosity in the liquid state.

As the sealing material 140, a silicone sealing material is particularly preferable.

It is preferable to provide cover members 120, 120 for concealment at the periphery of the connection portion 130 between the elastic wiring 1 and the extension wiring 110. Thereby, it is easy to suppress problems such as the periphery of the connection portion 130 of the composite wiring 100 becoming caught on fabric of a garment, and the appearance of the composite wiring 100 is also improved.

The cover member 120 only needs to be able to conceal the periphery of the connection portion 130 between the elastic wiring 1 and the extension wiring 110, and examples thereof include a heat shrinkable tube and a silicone tube. Further, the cover member 120 does not necessarily need to cover the periphery of the connection portion 130 of the extension wiring 110 widely, and the connection portion 130 can be covered by the connection member 40 whose surface is coated with an insulating material.

The method for producing the composite wiring 100 includes a method having the following steps (a) and (b):

Step (a): A step of supplying the sealing material 140 to the contact part of the conductor wire 12 of the elastic wiring 1 and the conductor wire 112 of the extension wiring 110.

Step (b): A step of caulking the contact portion of the conductor wire 12 of the elastic wiring 1 and the conductor wire 112 of the extension wiring 110 to form the connection portion 130.

Figure 4A:
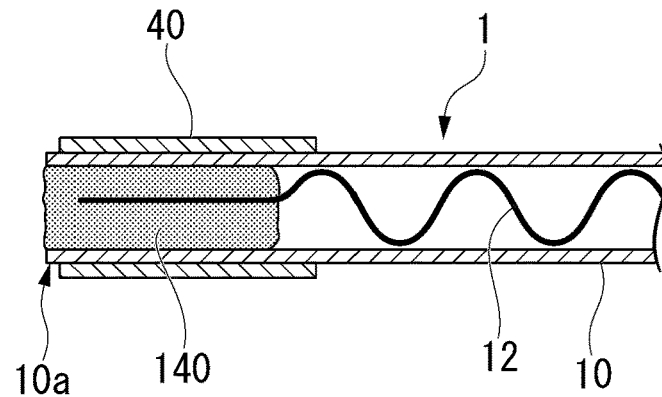
FIG. 4A is a cross-sectional view showing a production step of the composite wiring of FIG. 1.

In step (a), for example, as shown in FIG. 4A, the first end 10a side of the tube 10 is passed through the connection member 40, and the sealing material 140 is filled into the tube 10 where the connection member 40 is attached. At this time, the sealing material 140 may also be filled in the gap between the connection member 40 and the tube 10.

Next, as shown in HG 4B, the conductor wire 112 drawn from the extension wiring 110 is inserted into the portion of the tube 10 filled with the sealing material 140, and the conductor wire 12 of the elastic wiring 1 and the conductor wire 112 of the extension wiring 110 are brought into contact.

Figure 4B:
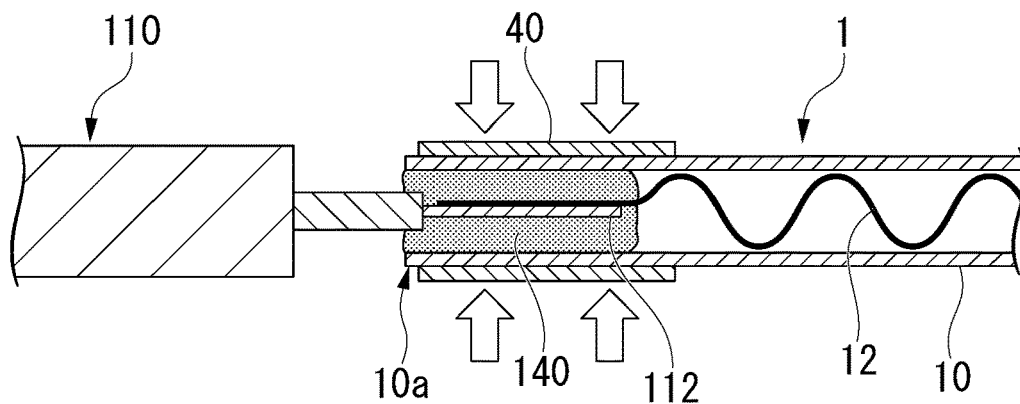
FIG. 4B is a cross-sectional view showing a production step of the composite wiring in FIG. 1.
Figure 4C:
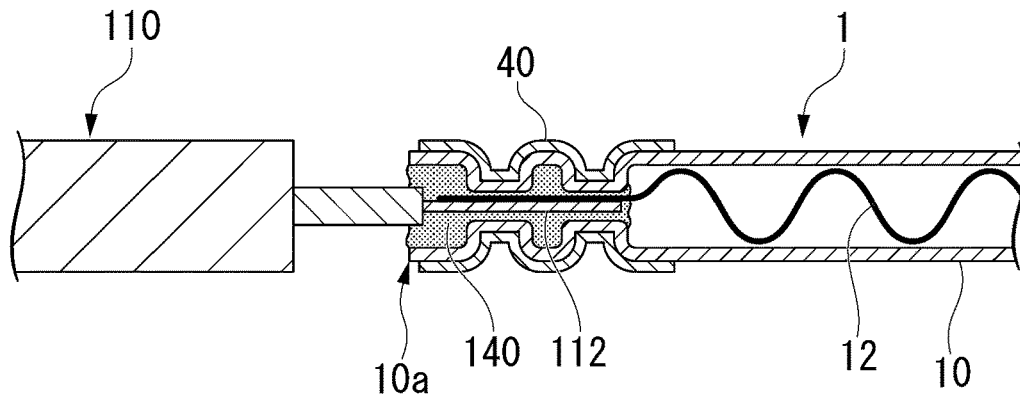
FIG. 4C is a cross-sectional view showing a production step of the composite wiring of FIG. 1.

In step (b), as shown in FIG. 4B, for example, the connection member 40 is partially crushed with a crimping tool or the like, and the conductor wire 12 of the elastic wiring 1 and the conductor wire 112 of the extension wiring 110 are caulked together with the tube 10. As a result, as shown in FIG. 4C, the connection portion 130 is formed in which the conductor wire 12 of the elastic wiring 1 and the conductor wire 112 of the extension wiring 110 are caulked and connected in a state of being sealed in a watertight manner with the sealing material 140.

After forming the connection portion 130, as shown in FIG. 2, the cover member 120 is attached to cover the periphery of the connection portion 130.

Similarly, on the second end portion 10b side of the tube 10 in the elastic wiring 1, the steps (a) and (b) are performed in the same manner to form the connection portion 130, and connect the elastic wiring 1 and the extension wiring 110. As shown in FIG. 3, the connection on the second end portion 10b side is performed in a state of applying a load to the tube 10 that pulls in the length direction extend the tube 10. By releasing the load that pulls the tube 10 after connection, the tube 10 returns to the original state of not being extended, and the composite wiring 100 as shown in FIG. 1 is obtained.

In addition, the order of a step (a) and step (b) is not limited to the order of performing step (b) after performing step (a), and step (a) may be performed after step (b). For example, after the contact portion between the conductor wire 12 of the elastic wiring 1 and the conductor wire 112 of the extension wiring 110 is caulked by the connection member 40, the sealing material 140 may be supplied to the contact portion by coating or the like to seal the connection portion 130 in a watertight manner.

As described above, in the composite wiring of the present invention, the conductor wire of the elastic wiring and the conductor wire of the extension wiring (other wiring) are connected by caulking in a state of being brought into contact with each other, and the connection portion is sealed in a watertight manner with a sealing material. Therefore, the composite wiring of this invention has excellent waterproofness at the connection portion between the conductor wire of the elastic wiring and the extension wiring.

The composite wiring of the present invention is not limited to the composite wiring 100 described above.

In the composite wiring 100, both sides of the elastic wiring 1 are connected to the extension wiring 110. However, for example, only the first end portion 10a side of the tube 10 in the elastic wiring 1 may be connected to the extension wiring 110, while the second end portion 10b side of the tube 10 need not be connected to the extension wiring 110.

The number of elastic wirings provided in the composite wiring of the present invention is not limited to one and may be two or more. The number of extension wirings (other wirings) providing in the composite wiring of the present invention is not limited to two, and may be one or three or more. The number of elastic wirings and extension wirings (other wirings) in the composite wiring of the present invention can be set as appropriate according to the application.

Figure 5:
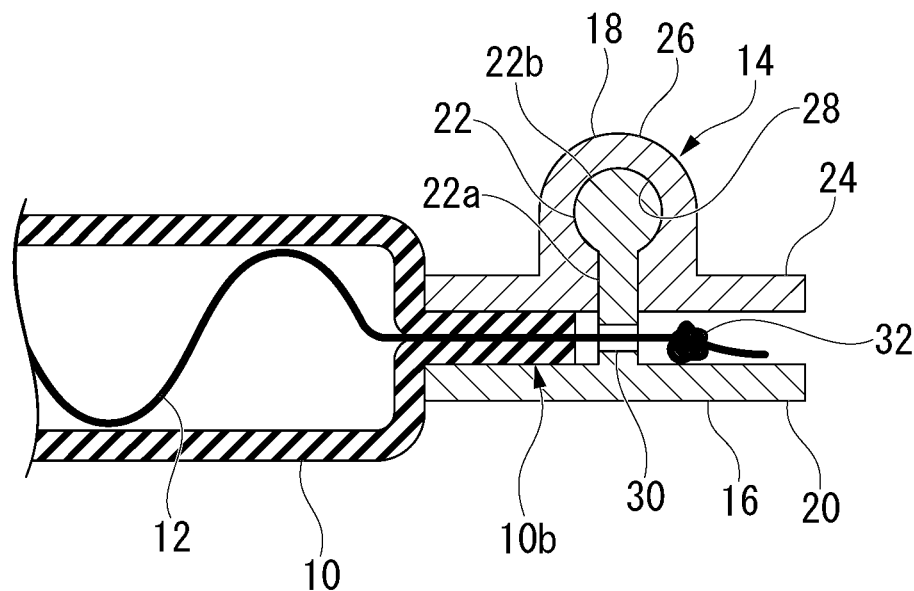
FIG. 5 is a cross-sectional view showing a caulking member provided on the second end side of the elastic wiring used in the composite wiring of FIG. 1.

When one end of the elastic wiring 1 is not connected to the extension wiring 110, the conductor wire 12 and the tube 10 are fixed without using the connection member 40 at the end of the elastic wiring that is not connected to the extension wiring. A mode in which the conductor wire and the tube are fixed at one or both ends of the elastic wiring without using a connection member connecting the elastic wiring and the extension wiring includes for example a mode using the caulking member 14 illustrated in FIG. 5.

The caulking member 14 is provided with a male member 16 and a female member 18.

The male member 16 is provided with a disk-shaped first flat plate portion 20 and a fitting convex portion 22 provided so as to rise from the central portion of the first flat plate portion 20. The fitting convex portion 22 is provided with a trunk portion 22a that rises from the first flat plate portion 20, and a spherical head portion 22b that is provided at the tip of the trunk portion 22a.

The female member 18 is provided with a disk-shaped second flat plate portion 24 and a protrusion 26 provided at the center of the second flat plate portion 24, with a fitting concave portion 28 being formed in the protrusion 26. The fitting concave portion 28 opens at the lower surface of the second flat plate portion 24. The fitting concave portion 28 of the female member 18 is adapted to fit the head portion 22b of the fitting convex portion 22 of the male member 16.

In this way, the male member 16 and the female member 18 are configured such that the fitting convex portion 22 and the fitting concave portion 28 are detachably fitted.

For example, at the second end portion 10b side of the tube 10, the tube 10 and the conductor wire 12 are caulked and fixed by the fitting convex portion 22 and the fitting concave portion 28 being fitted together so that the tube 10 and the conductor wire 12 are sandwiched by the first flat plate portion 20 of the male member 16 and the second flat plate portion 24 of the female member 18.

In that the tube and the conductor wire can be easily and securely fixed, it is preferable that the conductor wire and the tube be caulked and fixed by the caulking member as in this example. Moreover, it is more preferable that the conductor wire and the tube be caulked by the first flat plate portion of the male member and the second flat plate portion in a state where the male member and the female member of the caulking member are fitted together.

In this example, a through hole 30 is formed in the trunk portion 22a of the fitting convex portion 22 of the male member 16. A portion of the conductor wire 12 exposed from the tube 10 is passed through the through hole 30, and a knot 32 larger than the through hole 30 is formed on the distal side of the conductor wire 12 that has passed through the through hole 30. In this state, the conductor wire 12 and the tube 10 are caulked by the male member 16 and the female member 18.

In this way, it is preferable to caulk the conductor wire and the tube in a state of the portion of the conductor wire exposed from the end of the tube being passed through the through hole of the caulking member, and a knot larger than the through hole being formed at the portion of the conductor wire that has passed through the through hole.

By passing the distal end side of the conductor wire 12 through the through hole 30 of the fitting convex portion 22 and forming the knot 32 thereon as in this embodiment, it is possible to prevent unexpected pullout of the conductor wire 12 when fixing the conductor wire 12 and the tube 10, and stably arrange the conductor wire 12 between the male member 16 and the female member 18. Therefore, the conductor wire 12 and the tube 10 can be more easily fixed by the caulking member 14, leading to an improved yield.

The material for forming the caulking member 14 is not particularly limited, and examples thereof include stainless steel (SUS), brass, copper, iron, silver, gold, platinum, aluminum, and tin. By forming the caulking member 14 with metal, it is possible to use the caulking member 14 as a male connector that electrically connects to other members.

As the caulking member 14, for example, a snap button can be adopted.

When the end of one side of the elastic wiring 1 is not connected to the extension wiring 110, the caulking member 14 can be used as a female connector, as described below, in addition to the caulking member 14 as a male connector as described above.

Figure 10:
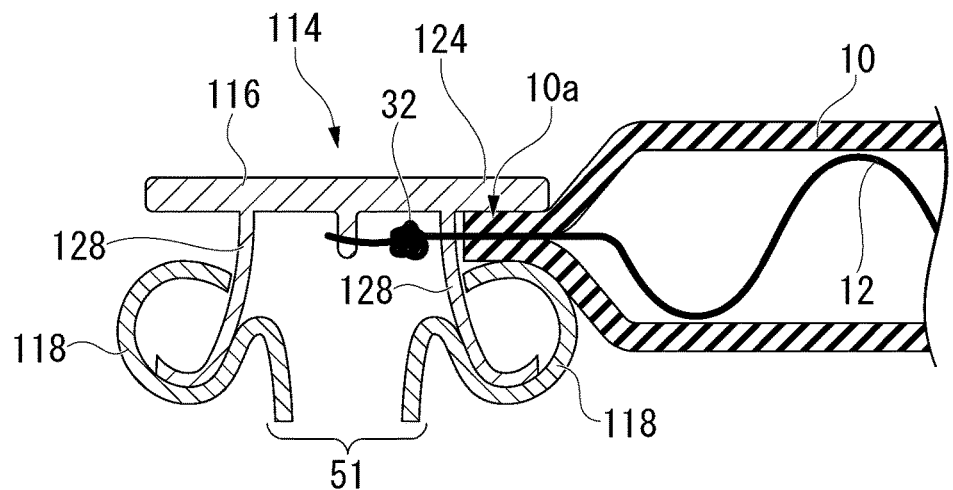
FIG. 10 is a cross-sectional view showing another example of a caulking member provided on the second end side of the elastic wiring used in the composite wiring of FIG. 1.

That is, referring to FIG. 10, a caulking member 114 includes a ring-shaped male member 116 and a ring-shaped female member 118. The female member 118, which has a spring property, is fixed to the ring-shaped male member 116 by being crimped to a spike 128 formed on the male member 116. The ring-shaped male member 116 has a ring-shaped flat plate portion 124. The spike 128 is formed so as to extend substantially perpendicularly to the flat plate portion 124. The female member 118 is caulked against the male member 116, thereby pressing the end portion 10a of the tube 10 sandwiched between the flat plate portion 124 and female member 118 onto the flat plate portion 124. That is, the female member 118 presses the end portion 10a of the tube 10 against the flat portion 124 by the spring force of the spike 128 and the female member 116. Thereby, the tube 10 and the conductor wire 12 are fixed by the female member 118 and the flat plate portion 124.

The knot 32 is formed on the conductor wire 12 drawn from the tube 10. The knot 32 is arranged at the center of the ring-shaped male member 116 with respect to the spike 123 to prevent the conductor wire 12 and the tube 10 from coming off the male member 116.

The ring-shaped female member 118 and the ring-shaped male member 116 are made of metal. Therefore, with the above configuration, the conductor wire 12 is electrically connected to the female member 118 via the male member 116. The female member 118 has a recess 51 at the center. This recess 51 is engaged with the protrusion 26 of the male connector shown in FIG. 2, thereby electrically connecting the male connector shown in FIG. 5 and the female connector shown in FIG. 10.

The mode of fixing the tube and the conductor wire in the elastic wiring is not limited to a mode using the caulking member 14. The elastic wiring may be one in which the tube and the conductor wire are caulked and fixed by a caulking member in which the through hole 30 is not formed in the male member 16 of the caulking member 14.

Figure 6:
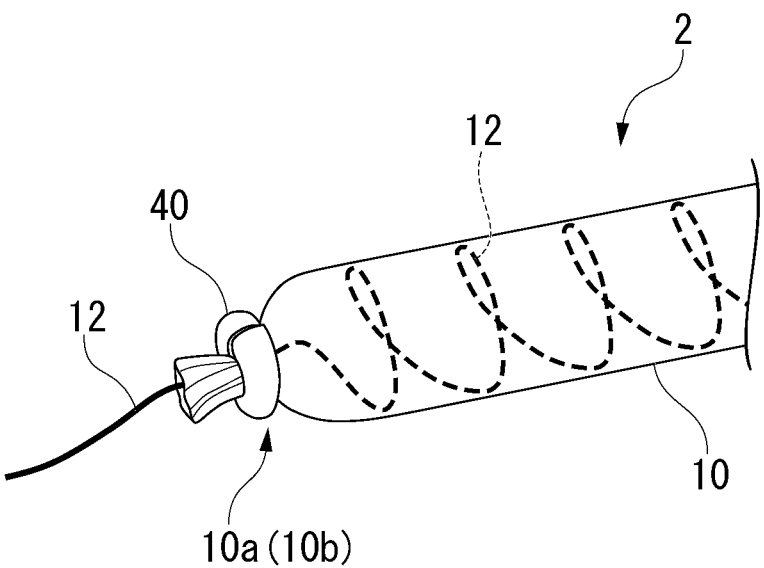
FIG. 6 is a perspective view showing another example of the elastic wiring used for the composite wiring according to one embodiment of the present invention.

In the elastic wiring, the conductor wire and the tube may be fixed by being stopped with a stopper at one or both ends. For example, as shown in FIG. 6, the tube 10 and the conductor wire 12 may be fixed by being stopped by a stopper 42 on one or both of the first end 10a side and the second end 10b side.

The stopper 42 is a rod-like fitting, being deformed into an annular shape so as to stop the conductor wire 12 and the tube 10.

Examples of the metal constituting the stopper 42 include SUS, brass, iron, and aluminum. The metal constituting the stopper 42 may be one type or two or more types.

The length and thickness of the stopper 42 may be set as appropriate as long as the conductor wire 12 and the tube 10 can be firmly fixed.

Figure 7:
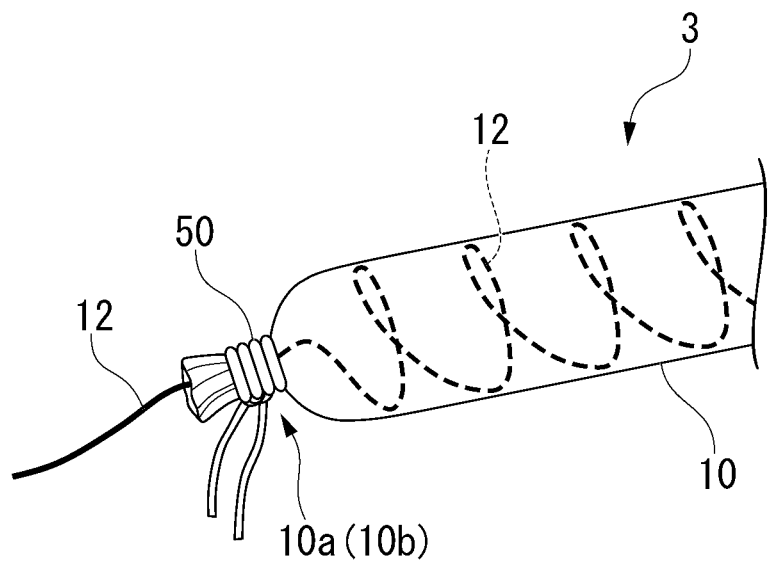
FIG. 7 is a perspective view showing still another example of the elastic wiring used for the composite wiring according to one embodiment of the present invention.

In the elastic wiring, the conductor wire and the tube may be bound and fixed by a band material at one or both of both end portions. For example, as shown in FIG. 7, the tube 10 and the conductor wire 12 are bound together and fixed by a band material 50 being wound around one or both of the first end portion 10a side and the second end portion 10b side.

As the form of the band material 50, any material can be used provided the band material 50 can bind and fix the conductor wire and the tube, and examples thereof include a binding band and a string. As the band material 50, one type may be used independently or two or more types may be used together.

The material for forming the band member 50 is not particularly limited, and examples thereof include polyethylene, polyethylene terephthalate, polyurethane, polystyrene, nylon, polycarbonate, fluorine resin, silicone rubber, and metals such as SUS, brass, iron, and aluminum.

The length and thickness of the band member 50 may be set as appropriate as long as the conductor wire 12 and the tube 10 can be firmly fixed.

The elastic wiring may be one in which a tube and a conductor wire are fixed by crimping using a crimping terminal. The crimping terminal is not particularly limited as long as the tube and the conductor wire can be fixed by crimping, and a known crimping terminal usually used for wiring can be employed.

Figure 8:
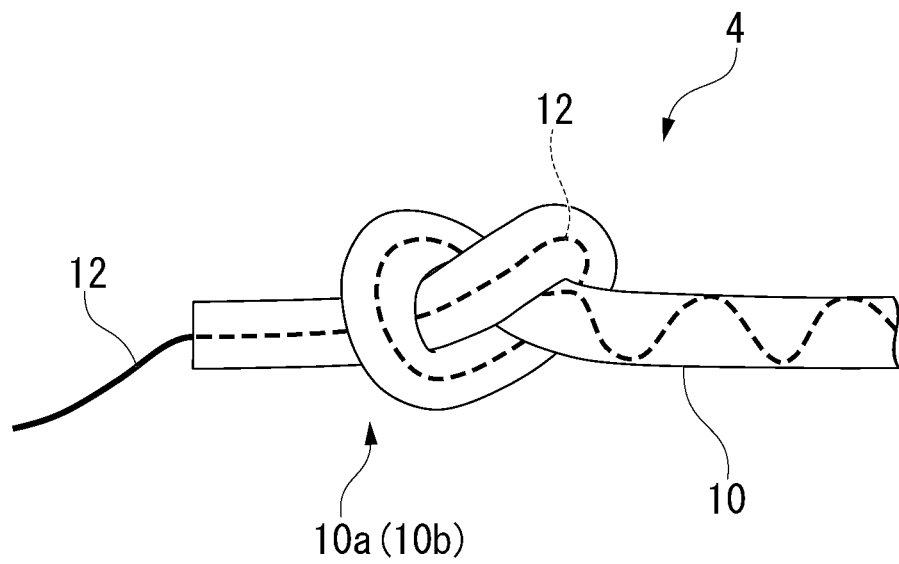
FIG. 8 is a side view showing yet still another example of the elastic wiring used for the composite wiring according to one embodiment of the present invention.

As shown in FIG. 8, in the elastic wiring, the tube 10 and the conductor wire 12 may be fixed by one or both portions of the tube 10 on the first end portion 10a side and the second end portion 10b side in the lengthwise direction thereof being respectively knotted together with the conductor wire 12.

The tube and the conductor wire may also be fixed by a pin terminal being inserted into both ends of the tube in the lengthwise direction thereof, with the portions of the tube in which the pin terminal has been inserted being bound with a string. The pin terminal is not particularly limited, and a publicly known crimping terminal normally used for wiring can be used.

As a mode of fixing the tube and the conductor wire in the elastic wiring, two or more of the above-described modes may be combined.

In the elastic wiring, the tube and the conductor wire may be fixed not only at both end portions of the tube but also at portions other than both end potions in the lengthwise direction of the tube. That is, the number of fixing portions at which the tube and the conductor wire in the elastic wiring are fixed is not limited to two, and may be three or more.

The composite wiring 100 can be suitably used for a wearable bio-signal acquisition device such as a belt-type or clothing-type wearable bioelectrode. For example, the composite wiring 100 can be used in such a manner that the extension wiring 110 is arranged at a place where a sense of discomfort is unlikely to arise at the time of wearing, with the portion where discomfort is likely to occur being relayed by the elastic wiring 1.

Figure 11:
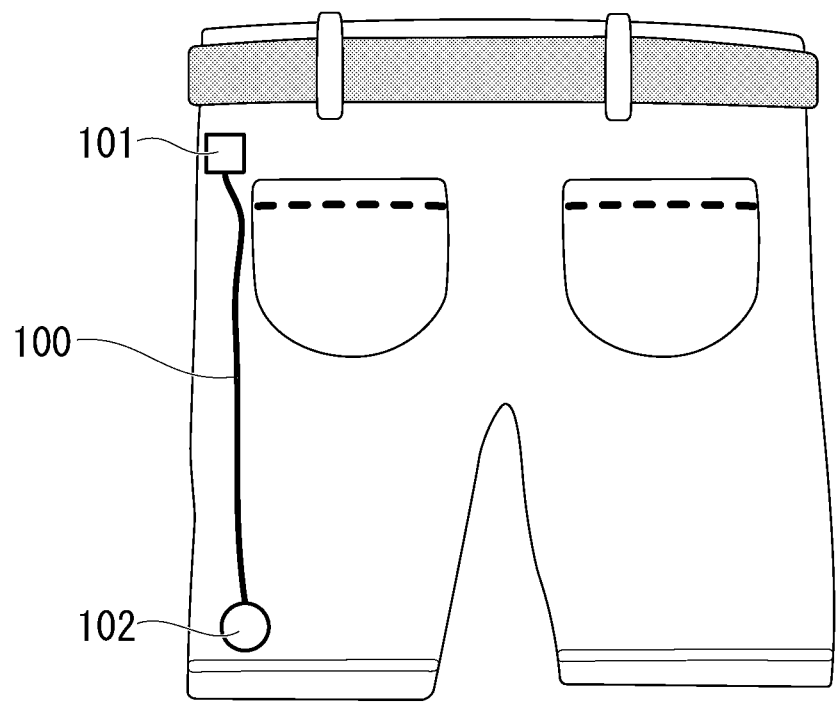
FIG. 11 is a front view showing a garment equipped with the composite wiring of one embodiment of the present invention.

FIG. 11 is a schematic view of the composite wiring 100 being fixed to a garment. Both ends of the composite wiring 100 connect a transmitter 101 and a sensor 102, respectively.

Here, in addition to the trousers shown in FIG. 11, the garment may be of any type such as a muffler, bandage, or a sock, as long as the wiring of the present invention can be fixed thereto, and any method of fixing the wiring may be used. In addition, as the sensor 102, any sensor may be chosen as appropriate, such as a wearable electrode, a pulse sensor, a thermometer, and an accelerometer, and the number and types of sensors may be a plurality.

For example, when using a pulse sensor, the pulse data measured by the sensor 102 can be transferred to the outside by the transmitter 101. While the composite wiring 100 may be arranged either on the inside or outside of the garment, if arranged on the inside, the wiring is not visible, and so the garment can be used as smart wear that acquires biometric data without the wearer being aware of the wiring.

The fixing method and fixing position of the transmitter 101 and the sensor 102 may be arbitrarily determined. For example, fixing to different garment is possible, in which the transmitter 101 is fixed to trousers and the sensor 102 is fixed to socks.

Further, in the elastic wiring and the composite wiring of the present invention, it is possible to wash the wear to which the composite wiring is applied by using SUS thread as the conductor wire. In addition, since elastic wiring and composite wiring using a tube made of silicone rubber is excellent in heat resistance and chemical resistance, clothing to which the elastic wiring is applied can be used in harsh environments as fire-resistant, incombustible and chemical resistant wear.

[Signal Acquisition Member]

A signal acquisition member according to a second aspect of the present invention is provided with a wiring and an electrode connected to a conductor wire of the wiring. In the signal acquisition member according to the second aspect of the present invention, the conductor wire and the electrode are caulked and connected, and the connection portion is sealed in a watertight manner with a sealing material.

Hereinbelow, an example of the signal acquisition member according to the second aspect of the present invention will be described with reference to an example.

Figure 9:
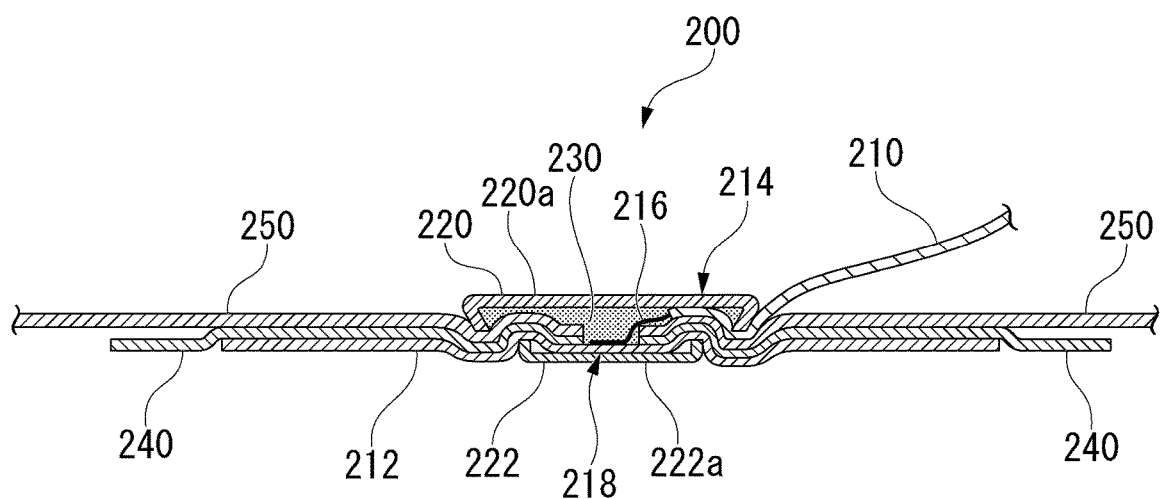
FIG. 9 is a cross-sectional view showing a signal acquisition member according to one embodiment of the present invention.

As shown in FIG. 9, a signal acquisition member 200 of this embodiment is provided with a wiring 210, an electrode 212, and a connection member 214. In the signal acquisition member 200, a connection portion 218 between a conductor wire 216 of the wiring 210 and the electrode 212 is caulked by the connection member 214.

The wiring 210 is not particularly limited, and may be the elastic wiring described in the composite wiring, or may be a publicly known wiring other than the elastic wiring. The elastic wiring is preferable in that the electrode 212 is less prone to bending after the wiring 210 is connected, and noise in signal acquisition is easily reduced.

The electrode 212 is not particularly limited, and examples thereof include a conductive polymer electrode fixed in a state in which a fiber sheet is impregnated with a conductive polymer. A publicly known electrode other than the conductive polymer electrode may also be used.

The fiber constituting the fiber sheet is not particularly limited, and examples thereof include synthetic fibers such as nylon fibers and polyester fibers, vegetable fibers such as cotton and hemp, and animal fibers such as silk and wool.

The conductive polymer is not particularly limited, and may be a polythiophene-based polymer such as PEDOT (poly (3,4-ethylenedioxythiophene)), or polypyrrole, polyaniline, polyacetylene, polyparaphenylene, polyparaphenylenevinylene, polyfluorene and the like.

The connection member 214 is provided with a pair of first and second crimping members 220 and 222 having a U-shaped cross section. The first crimping member 220 is one size larger than the second crimping member 222, and when caulking the connection portion 218 of the wiring 210 and the electrode 212, the second crimping member 222 is designed to enter into the first crimping member 220.

Examples of the material forming the first crimping member 220 and the second crimping member 222 include metals such as stainless steel (SUS), brass, copper, iron, silver, gold, platinum, aluminum, and tin.

It is preferable that an outer surface 220a of the first crimping member 220 and an outer surface 222a of the second crimping member 222 be coated with an insulating material.

In this example, a waterproof sheet 240 and a fabric 250 are stacked in this order on the electrode 212 so that a part of the surface of the electrode 212 is exposed, and a conductor wire 216 drawn from the wiring 210 is brought into contact with the exposed surface of the electrode 212. In this state, the first crimping member 220 and the second crimping member 222 are crimped from above and below, whereby the connection portion 218 between the wiring 210 and the electrode 212 is formed.

In the signal acquisition member 200, the connection portion 218 caulked by the connection member 214 is sealed with a sealing material 230 in a watertight manner.

Specifically, in this example, the sealing material 230 is filled on the electrode 212, around the contact portion between the conductor wire 216 of the wiring 210 and the electrode 212, on the inner side of the first crimping member 220 of the connection member 214, whereby the conductor wire 216 of the wiring 210 and the connection portion 218 of the electrode 212 are sealed in a watertight manner.

Thereby, the connection portion 218 between the wiring 210 and the electrode 212 has excellent waterproofness.

As the sealing material 230, the same as those listed for the sealing material 140 of the composite wiring 100 can be used, with a silicone sealing material being preferable.

The material forming the waterproof sheet 240 may be any material that is insulating and waterproof, and examples thereof include polyethylene terephthalate, polyvinyl chloride, polyethylene, and polypropylene. As the waterproof sheet 240, a deposition film in which a metal such as aluminum, silver, or copper is deposited may be used.

A method for producing the signal acquisition member 200 includes a method having the following steps (x) and (y).

Step (x): A step of supplying the sealing material 230 to the contact portion between the conductor wire 216 of the wiring 210 and the electrode 212.

Step (b): A step of forming the connection portion 218 by caulking the contact portion between the conductor wire 216 of the wiring 210 and the electrode 212.

In step (x), for example, the waterproof sheet 240 and the fabric 250 are stacked in this order on the electrode 212 so that a part of the surface of the electrode 212 is exposed. Further, the sealing material 230 is supplied to the portion of the conductor wire 216 drawn from the wiring 210. Then, the conductor wire 216 of the wiring 210 is brought into contact with the exposed portion of the surface of the electrode 212. Alternatively, the conductor wire 216 of the wiring 210 may be brought into contact with the exposed portion of the surface of the electrode 212, and then the sealing material 230 may be supplied to the contact portion.

In step (b), the first crimping member 220 of the connection member 214 is arranged on the upper side of the contact portion between the electrode 212 and the conductor wire 210 of the wiring 210, and a second crimping member 222 is arranged at a position corresponding to the contact portion between the electrode 212 and the conductor wire 210 of the wiring 210 on the lower side of the electrode 212. Next, the first crimping member 220 and the second crimping member 222 are press bonded from above and below, and the electrode 212 and the conductor wire 216 of the wiring 210 are caulked to form the connection portion 218.

The order of step (x) and the step (y) is not limited to the order in which step (x) is performed and then the step (y) is performed. Step (x) may be performed after performing step (y), as long as the effect of the present invention is not impaired. For example, after the contact portion between the electrode 212 and the conductor wire 216 of the wiring 210 is caulked by the connection member 214, the sealing material 140 may be supplied from around the connection portion 218 and sealed in a watertight manner.

In the case where the above-described elastic wiring is used as the wiring 210, the connection between the conductor wire of the wiring and the electrode by the connection member may also serve as the fixing of the conductor wire and the tube at the end of the elastic wiring. Thereby, since the number of work steps decreases, the productivity of the signal acquisition member improves.

The signal acquisition member 200 can be particularly suitably used for a wearable bio-signal acquisition device such as a wearable bioelectrode. The use of the signal acquisition member of the present invention is not limited to a wearable bio-signal acquisition equipment.

As described above, in the signal acquisition member of the present invention, the conductor wire of the wiring and the electrode are caulked and connected by the connection member, and that connection portion is sealed in a watertight manner with the sealing material. Therefore, the waterproofness of the connection portion between wiring and an electrode is excellent in the signal acquisition member of the present invention.

Note that the signal acquisition member of the present invention is not limited to the signal acquisition member 200 described above.

For example, the signal acquisition member of the present invention may be configured such that when the connection portion between the electrode and the wiring is caulked and connected by the connection member, the fabric or waterproof sheet is not disposed on the connection portion.

DESCRIPTION OF THE REFERENCE SYMBOLS

- 1: Elastic wiring
- 10: Tube
- 10a: First end portion
- 10b: Second end portion
- 12: Conductor wire
- 40: Connection member
- 42: Stopper
- 50: Band material
- 100: Composite wiring
- 110: Extension wiring (other wiring)
- 112: Conductor wire
- 130: Connection portion
- 140: Sealing material
- 200: Signal acquisition member
- 210: Wiring
- 212: Electrode
- 214: Connection member
- 216: Conductor wire
- 218: Connection portion
- 220: First crimping member
- 222: Second crimping member
- 230: Sealing material
- 240: Waterproof sheet
- 250: Fabric

The invention claimed is:

1. A composite wiring comprising:
an elastic wiring comprising an elastic tube, a conductor wire disposed inside the tube, and first and second fixing portions that fix the conductor wire and the tube together at first and second ends of the tube, respectively, in a lengthwise direction thereof, a length of the conductor wire between the first and second fixing portions when the tube is in an unextended state being longer than the length of the tube between the first and second fixing portions;
other wiring separate from the elastic wiring; and
a connection member that connects the conductor wire of the elastic wiring and a conductor wire of the other wiring at least at the first fixing portion by caulking in a state of being brought into contact with each other, the connection member having an interior section sealed in a watertight manner with a sealing material,
wherein the connection member is a crimping sleeve, and the crimping sleeve connects the conductor wire of the elastic wiring and the conductor wire of the other wiring by caulking the conductor wire of the other wiring inserted in an end portion of the tube of the elastic wiring from the periphery of the tube of the elastic wiring.

2. The composite wiring according to claim 1, wherein the sealing material is a non-curing elastic sealing material.

3. A composite wiring comprising:
an elastic wiring comprising an elastic tube, a conductor wire disposed inside the tube, and first and second fixing portions that fix the conductor wire and the tube together at first and second ends of the tube, respectively, in a lengthwise direction thereof, a length of the conductor wire between the first and second fixing portions when the tube is in an unextended state being longer than the length of the tube between the first and second fixing portions;
other wiring separate from the elastic wiring; and
a connection member that connects the conductor wire of the elastic wiring and a conductor wire of the other wiring at least at the first fixing portion by caulking in a state of being brought into contact with each other, the connection member having an interior section sealed in a watertight manner with a sealing material,
wherein the second fixing portion includes a caulking member comprising:
a male member comprising a first flat plate portion and a fitting convex portion that is provided on the first flat plate portion; and
a female member comprising a second flat plate portion and a fitting concave portion that is provided on the second flat plate portion,
wherein, in a state of the fitting convex portion and the fitting concave portion being fitted together, the conductor wire and the tube are caulked by the first flat plate portion and the second flat plate portion, and a protrusion is formed in the female member.

4. A composite wiring comprising:
an elastic wiring comprising an elastic tube, a conductor wire disposed inside the tube, and first and second fixing portions that fix the conductor wire and the tube together at first and second ends of the tube, respectively, in a lengthwise direction thereof, a length of the conductor wire between the first and second fixing portions when the tube is in an unextended state being longer than the length of the tube between the first and second fixing portions;
other wiring separate from the elastic wiring; and
a connection member that connects the conductor wire of the elastic wiring and a conductor wire of the other wiring at least at the first fixing portion by caulking in a state of being brought into contact with each other, the connection member having an interior section sealed in a watertight manner with a sealing material,
wherein the second fixing portion includes a caulking member comprising:
a male member comprising a flat plate portion and a spike extending substantially perpendicularly from the flat plate portion; and
a ring-shaped female member fixed to the male member by being crimped to the spike,
wherein, by fixing the female member to the male member, the conductor wire and the tube are caulked by the flat plate portion and the female member, and a recess is formed in the ring-shaped central portion of the female member.

5. The composite wiring according to claim 3, wherein the sealing material is a non-curing elastic sealing material.

6. The composite wiring according to claim 4, wherein the sealing material is a non-curing elastic sealing material.

* * * * *